United States Patent [19]

Hom et al.

[11] Patent Number: 4,800,083
[45] Date of Patent: * Jan. 24, 1989

[54] SUSTAINED RELEASE METHOD AND PRODUCT

[75] Inventors: Foo S. Hom, Safety Harbor; William R. Ebert, St. Petersburg, both of Fla.

[73] Assignee: R. P. Scherer Corporation, Troy, Mich.

[*] Notice: The portion of the term of this patent subsequent to Jan. 31, 2001 has been disclaimed.

[21] Appl. No.: 921,069

[22] Filed: Oct. 20, 1986

[51] Int. Cl.[4] ........................... A61K 9/52; A61K 9/68
[52] U.S. Cl. ....................................... 424/457; 419/48; 419/452; 419/456
[58] Field of Search .................. 424/48, 452, 456, 457

[56] References Cited

U.S. PATENT DOCUMENTS

| | | | |
|---|---|---|---|
| 3,126,321 | 3/1964 | Kurtz | 167/83 |
| 3,851,051 | 11/1974 | Miskel et al. | 424/37 |
| 3,867,521 | 2/1975 | Miskel et al. | 424/37 |
| 4,105,779 | 8/1978 | Kobayashi et al. | 424/78 |
| 4,169,885 | 10/1979 | Raaf et al. | 424/16 |
| 4,428,927 | 1/1984 | Ebert et al. | 424/37 |
| 4,434,153 | 2/1984 | Urquhart et al. | 424/22 |
| 4,532,126 | 7/1985 | Ebert et al. | 424/48 |

FOREIGN PATENT DOCUMENTS 888683 12/1971 Canada .

Primary Examiner—Shep K. Rose
Attorney, Agent, or Firm—Alllegretti & Witcoff, Ltd.

[57] ABSTRACT

A capsule product and method for gradually releasing a medicament for absorption to a body of a warm blooded animal through the gastrointestinal system. The capsule has a fill material which includes a masticatory substance and a medicament that is dispersed throughout the gum. The medicament is of a type that is effectively and desirably released for absorption by the body through the gastrointestinal tract over an extended period of time. The masticatory substance forms a supporting cohesive matrix for the medicament. The gelatin shell, usually formed from gelatin, water, and a plasticizer, formed around the fill material into a capsule of a size and shape to be readily swallowable. Upon swallowing, the gelatin shell is rapidly dissolved in the gastrointestinal juices, while the fill material is substantially insoluble in the gastrointestinal juices. The matrix having the medicament dispersed throughout is subjected to substantially continuous random motion while contained within the gastrointestinal juices, while at body temperatures, and while under the influence of peristaltic movement for substantially varying the exposed surface area of the fill. As the surface area of the fill material is being changed, the medicament is gradually released from the exposed surface area for an extended period of time for ultimate absorption of the drug by the body.

49 Claims, 3 Drawing Sheets

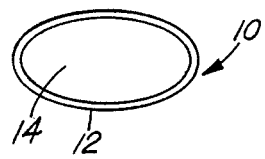
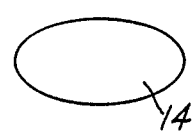 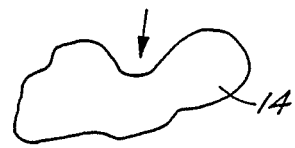
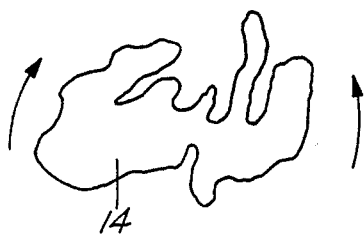 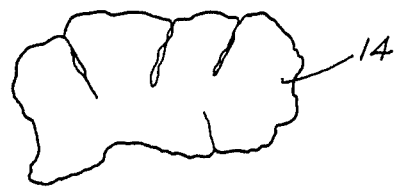

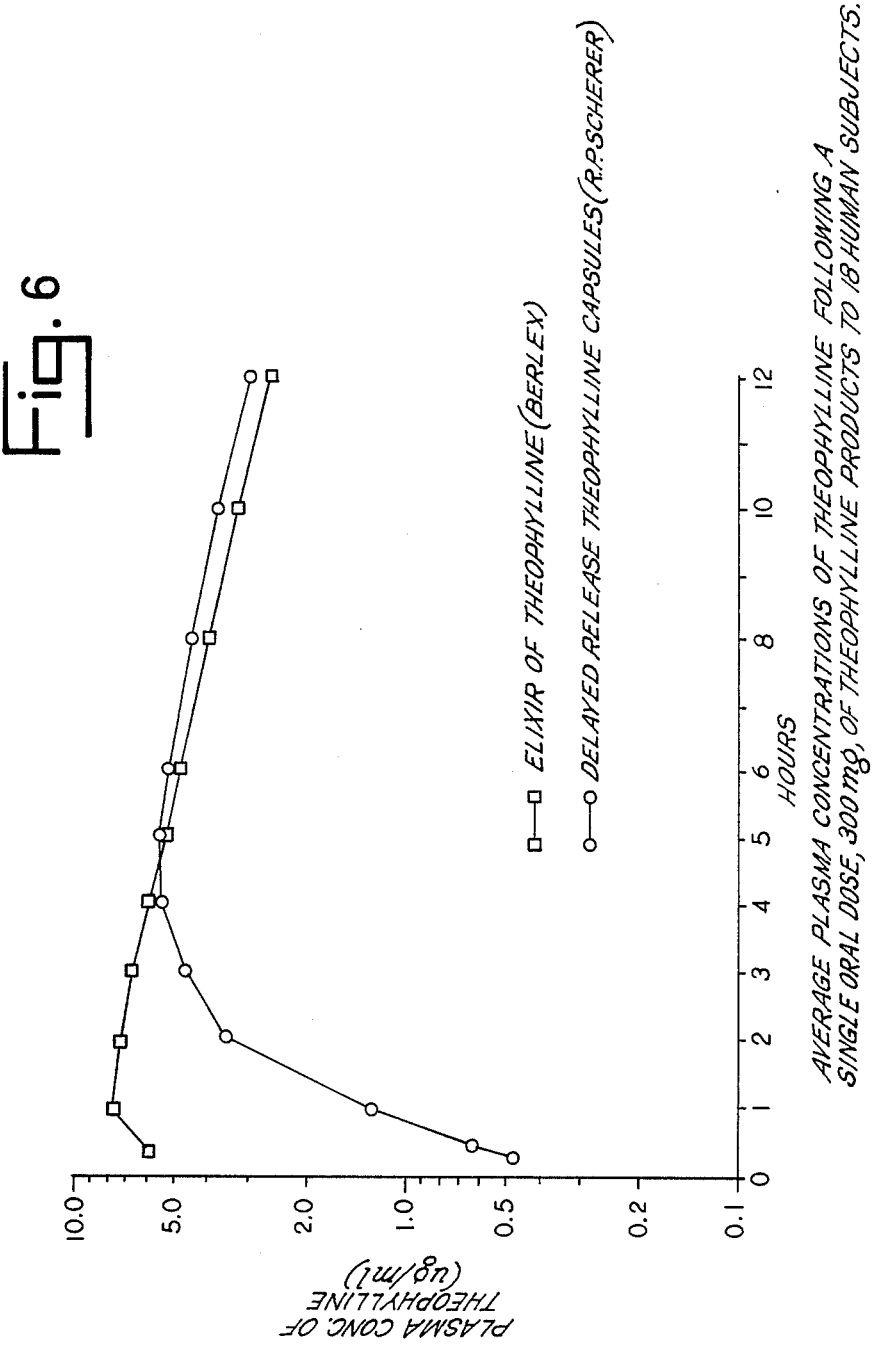

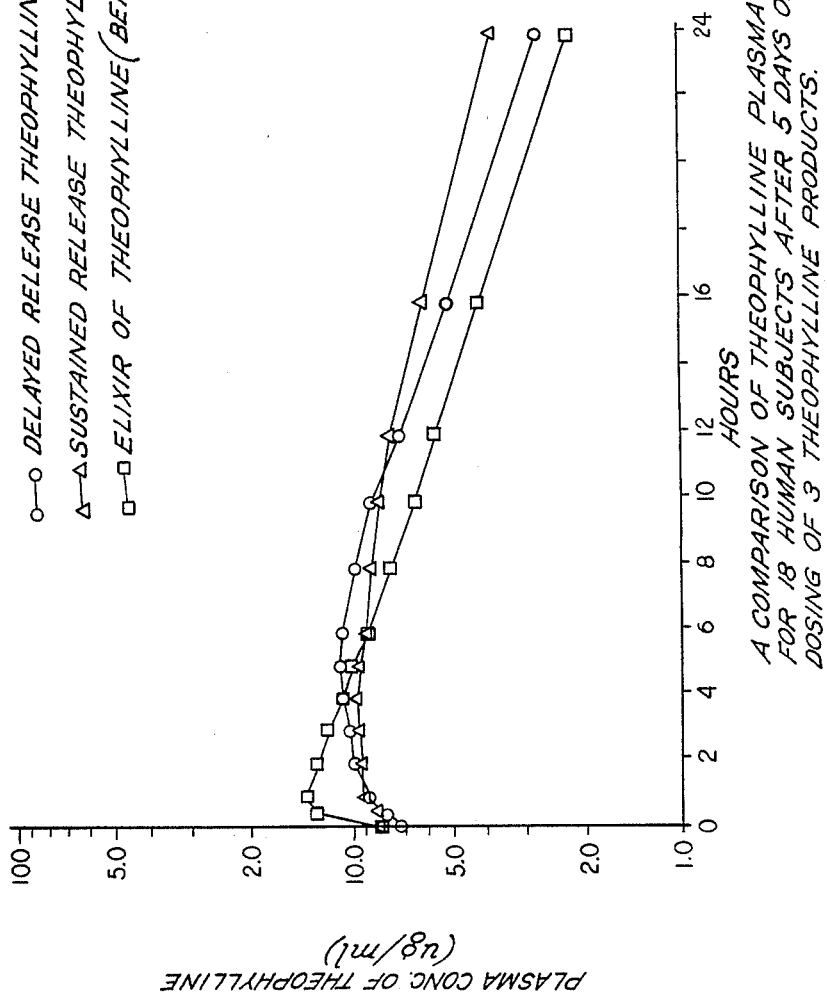

SUSTAINED RELEASE METHOD AND PRODUCT

BACKGROUND OF THE INVENTION

Field of the Invention and Description of the Prior Art

This invention relates to an improved sustained release product and method used for administering drugs to warm blooded animals and it particularly relates to a gelatin capsule product and method for gradually releasing a drug, contained in the fill material of the capsule, to warm blooded animals; the invention more specifically relates to an improved sustained release soft elastic drug form and method of administration.

Generally speaking, orally administered drug dosage forms include elixirs or drugs administered as liquids, compressed tablets, compressed coated tablets, hard shell gelatin capsules, and soft shell gelatin capsules, all of which contain unit dosage amounts of a selected drug. The dosage regimen for drugs that are orally administered quite commonly requires a predetermined schedule of two, three or four times a day, of the unit dosage forms of the drug. It can be generally said that, with many drugs, the administration of the drug or medicament to the patient in one or two doses per day, while ensuring substantially constant blood levels with adequate drug bioavailability, is highly desirable. This is the reason for the desirability of having so-called sustained release drug dosage forms, that is, dosage forms which enable the drug to be released to the body of a warm blooded animal over an extended and generally pre-determined period of time.

Although a dosage regimen involving one or two oral doses of the drug per day is consideredto be highly desirable, not all drugs are logical candidates for a sustained release dosage form. Generally speaking, drugs having a relatively short half life, for example, less than about 8–10 hours, are good candidates for sustained release drug dosage forms. The purpose of having a sustained release dosage form for a drug is to generally flatten the plasma conconcentration curve, that is, reduce the concentration level of the drug in the plasma immediately or shortly after administration so as to attain a fairly constant plasma level for the drug. On the other hand, there is no rational basis for having sustained release preparations for drugs having a long biological half life, such as twelve hours or more. Similarly, highly potent drugs are not generally reasonable candidates for sustained release drug forms since it is desirable to have the option to withhold the drug at will during the dosage regimen so that control is not lost when the patient is under continuous medication.

Sustained release dosage forms have generally been used with hard gelatin capsules having enteric coated microcapsules therein or compressed into tablets and with coated tablets, but have generally not been used with soft gelatin capsules which are usually filled with a liquid or a flowable substance, thereby making a sustained release dosage form, as a practical matter, almost impossible. Canadian Pat. No. 888,683 relates to a sustained release soft elastic gelatin (SEG) capsule dosage form in which the capsule filling, upon coming in contact with water or with the juices of the gastrointestinal tract, forms a microporous, spongy substance, including the medicament, which gives off the active substance, continuously, through diffusion for absorption into the ambient medium.

Although the sustained release drug form disclosed in this Canadian patent does relate to a possible sustained release system used in connection with gelatin capsules, there is a need and interest in the development of sustained release formulations that are encapsulated within gelatin capsules, particularly soft elastic gelatin capsules of the type normally containing a liquid or flowable substance. Although it is not difficult to develop theoretical equations that would describe the desired release characteristics of sustained action tablets and capsules, it is another matter to formulate and manufacture products that will predictably deliver a drug under conditions which are variable due to patient physiology and therapy and yet reflect the desired plasma level profiles designed into the dosage form.

SUMMARY OF THE INVENTION

It is therefore an important object of the present invention to provide a highly unique sustained release drug delivery system wherein the drug dosage form is swallowed and the drug is encapsulated within a soft or hard shell gelatin capsule.

It is also an object of the present invention to provide a highly unique sustained release drug delivery system particularly suitable for utilization of soft elastic gelatin capsule dosage forms.

It is a further object of the present invention to provide an improved sustained release drug delivery system wherein the drug is dispersed within a gum or elastomer matrix system which defines a fill material that is surrounded by a soft or hard shell gelatin capsule for oral administration and swallowing.

It is another object of the present invention to provide a highly unique sustained release drug delivery system particularly useful for the drug theophylline, in soft elastic gelatin capsule or hard shell gelatin capsule form.

It is still another important object of the present invention to provide a highly unique method for administering drugs, particularly adapted for sustained release administration over an extended period of time, utilizing a highly unique delivery system in which a gelatin capsule dosage form contains a fill material of a gum or elastomer defining a matrix for a drug dispersed therein.

It is also a further object of the present invention to provide a highly unique method for administering the drug theophylline over an extended period of time to a warm blooded animal by dispersing the drug theophylline in a gum or elastomer matrix which is encapsulated within a soft elastic gelatin capsule, then orally administered and swallowed.

It is still a further object of the present invention to provide a highly unique sustained release drug delivery system which involves encapsulation of a fill material of a drug in a gum or elastomer matrix of the type which is capable of being constantly deformed by peristaltic movement in the gastrointestinal system in order to continuously provide a new surface area for the fill material in order that a drug on the exposed surface area may be released by the surrounding medium and then absorbed by the body through the gastrointestinal system.

Further purposes and objects of the present invention will appear as the specification proceeds.

The foregoing objects are accomplished by providing a fill material of a masticatory gum or elastomer having a medicament dispersed substantially uniformly throughout a matrix, the medicament being of a type that is desirably and effectively released for absorption by the body of a warm blooded animal through the gastrointestinal tract over an extended period of time, the gum or elastomer forming a supporting matrix for the medicament, the gum or elastomer being substantially insoluble in the gastrointestinal juices, a shell of gelatin and water, with or without a plasticizer, a plasticizer, being formed around the fill material to define a filled capsule, the capsule being sized and shaped to be readily swallowable, the gelatin shell being substantially dissolved by the gastrointestinal juices, the fill material with a medicament dispersed therein being subjected to substantially constant random motion while in the gastrointestinal juices, while at body temperatures, and while under the influence of peristaltic movements in the gastrointestinal tract for continuously varying the exposed surface area of the fill material, so as to gradually release the medicament located in the exposed surface to the gastrointestinal juices for ultimate absorption by the body over an extended period of time.

BRIEF DESCRIPTION OF THE DRAWINGS

Referring to the accompanying drawings, there is provided a graphic illustration of the mechanism by which a drug in a fill material, encapsulated within the gelatin capsule results in the desired sustained release effect for the drug, and also there is provided graphs showing the drug release curves resulting from specific examples of the invention, wherein:

FIG. 1 is a cross sectional illustration of a soft elastic gelatin capsule dosage form enclosing a fill material wherein the capsule dosage form is made in accordance with the present invention;

FIG. 2 is an illustration of the fill material of the capsule of FIG. 1 after dissolution of the gelatin shell;

FIG. 3 is an illustration of the fill material after being softened by body temperature and, while under the influence of peristaltic movement and while being subjected to convolutions;

FIG. 4 is an illustration of new surface area exposure of the fill material of FIG. 3 following the initial convolutions illustrated in FIG. 3;

FIG. 5 shows the state of the fill mass following continuing convolutions thereof as the drug is being gradually released and the expanded matrix is in condition for excretion from the gastrointestinal system;

FIG. 6 illustrates the drug release curve for Example I; and

FIG. 7 illustrates the drug release curve for Example II.

DETAILED DESCRIPTION OF THE PREFERRED EMBODIMENT

Generally speaking, the present invention relates to a sustained release drug delivery system for oral administration, wherein the delivery system comprises an effective unit dosage amount of a drug capable of being absorbed into the blood of a warm blooded animal from the gastrointestinal tract. Preferably, the unit drug form is encapsulated as a fill material within a gelatin capsule, preferably a soft elastic gelatin (SEG) capsule as opposed to a two piece telescoping hard gelatin capsule. The capsule fill material generally comprises a masticatory substance, preferably a gum or elastomer, with a preselected drug or medicament dispersed substantially uniformly throughout the masticatory substance which defines a matrix for the drug.

Since not all medicaments are candidates for the sustained release form, the drug or medicament that is utilized in our invention is a type that is desirably and effectively gradually releasable for absorption by the body over an extended period of time. The masticatory substance itself defines a cohesive support matrix for the medicament. The gelatin shell of the capsule is rapidly dissolvable in the gastrointestinal juices while the capsule fill material, specifically the masticatory substance, is substantially insoluble in the gastric juices. The matrix has a formulation that is capable of being filled into the gelatin capsule. After swallowing, while in the presence of the gastrointestinal juices at body temperatures and while under the influence of the peristaltic movement of the gastrointestinal tract, the matrix is subjected to continuous random motion for substantially continuously varying the exposed surface area of the matrix. The medicament or drug is gradually released over an extended period of time from the exposed surface area as the surface area is being varied. In this way, the drug or medicament is gradually and ultimately absorbed by the body through the gastrointestinal tract while attaining suitable plasma concentration levels for the particular drug. Thus, the drug is released from the matrix for an extended period of time while in the gastrointestinal tract.

Our unique drug form or delivery system and method, providing a sustained release effect for absorption of drugs or medicaments, are useful for a wide range of drugs or drug categories including, but not limited to antihistamines, sedatives, tranquilizers, cardiovascular drugs, respiratory drugs (antiasthmatics, antitussives), sympathomimetic drugs, diuretic drugs, analgesics and antipyretics, antimotion sickness and antinauseants, and electrolytes and hematinics. Specific examples of such antihistamines are: chlorpheniramine maleate (such as Deconamine SR capsules by Berlex and Chlor-trimeton by Schering), brompheniramine maleate (such as Bromfed capsules by Muro and Dimetane tablets by A. H. Robins) and dexchlorpheniramine maleate (such as Polaraimine Repetabs by Schering). Suitable sedatives include doxylamine succinate (such as Unisom Nighttime Sleep-aid by Leeming), and promethazine hydrochloride (such as Remsed tablets by Endo). Suitable tranquilizers for use in our sustained release drug form include diazepam (such as Valrelease capsules by Roche), lithium carbonate (such as Eskalith CR tablets by Smith, Kline & French), and perphenazine (such as Trilafon Repetabs tablets by Schering). Cardiovasulcar drugs which may be utilized in our sustained release drug form include quinidine sulfate (such as in Quinidex Extentabs by A. H. Robins), nitroglycerin (such as Nitrostat SR capsules by Parke-Davis), propranolol hydrochloride (such as inderal by Ayerst), and nifedipine (such as in Procardia by Pfizer). Suitable antiasthmatics or antitussives include theophylline (such as Theo-Dur by Key Pharmaceuticals), guaifenesin (such as Congess SR & JR capsules by Fleming & Co.), dextromethorphan hydrobromide (such as Cotylenol tablets or capsules by McNeil Consumer Products), and codeine phosphate (such as Empirin with codeine tablets by Burroughs Wellcome Co.). Suitable sympathomimetic drugs useful in our sustained release drug form include ephedrine, (such as Quibron Plus by Mead Johnson Pharmaceuticals), Pseudoephedrine hydrochloride (such as Bromfed capsules by Muro Pharmaceuticals), and phenylpropanolamine hydrochloride (such as Histabid Duracap timed action capsules by Glaxo, Inc.). Diuretic drugs that are useful in our sustained release drug form include actazolamide (such as Diamox Sequels sustained release capsules by Lederle), and hydrochlorothiazide (such as Hydro Diuril tablets by Merck, Sharp & Dohme). Analgesics and antipyretics useful in our sustained release drug form include aspirin and indomethacin (such as Indocin SR capsules by Merck Sharp & Dohme). Suitable antimotion sickness and antinauseants include meclizine hydrochloride (such as Bonine tablets by Pfizer), dimenhydrinate (such as Dramamine tablets by Searle), hydroxyzine hydrochloride (such as Atarax tablets by Roerig), and prochlorperazine maleate (such as Compazine tablets by Smith, Kline & French). Electrolytes and hematinics useful in our sustained release drug form include potassium chloride (such as Micro-K Extencaps by Robins and Slow-K tablets by Ciba), and ferrous fumarate (such as Ferro-Sequels by Lederle).

In certain of the above-identified drugs, it is desirable to utilize enteric coatings to insure that the drug will remain intact in the stomach. Therefore, enteric coatings may be used with various drugs. The enteric coated drug microcapsules are dispersed throughout the matrix as is the drug itself. However, because of the enteric coating, the drug would normally not be released until the matrix leaves the stomach and passes into the intestine. The primary intention of an enteric coated drug is to delay release of the drug or inactivating the drug while in the stomach, for example, some drugs may cause nausea or bleeding by irritation of the gastric mucosa. Examples of such drugs are aspirin and steroids. Useful enteric coatings in manufacturing our coated drug forms include hydroxypropylmethylcellulose phthalate, cellulose acetate phthalate, polyvinyl acetate phthalate, methacrylic acid-methacrylic acid ester copolymers, cellulose acetate succinate, styrene-maleic acid polymer, amylose acetate phthalate, shellac, phenyl salicylate, and formalized gelatin.

The procedures for applying enteric polymers to drugs are well known. Suitable procedures for enteric coating of drugs include pan coating, air suspension coating, dip coating, compression coating, electrostatic coating, coacervationphase separation process coating, and multiorifice-centrifugal process coating. Since the particular methods used for forming the enteric coating are not considered a part of the present invention, reference is made to the literature, including, for example, *The Theory and Practice of Industrial Pharmacy*, by Lachman, Liebeman, and Kanig, pages 376-386.

All of the above drugs, whether enterically coated or not, are suitable candidates for our sustained release drug form or delivery system as all of the drugs have a half life of less than about 8-10 hours. Also, all of the drugs are capable of being absorbed into the blood of the gastrointestinal tract of warm blooded animals. The amount of the drug used in our drug form or delivery system and method may vary over a wide range although, generally, any therapeutically effective unit dosage amount of a selected drug is used.

As previously discussed, an important component of the fill material is an insoluble, cohesive masticatory substance, a gum or elastomer, which defines the matrix system for the medicament or drug which is entrapped in the matrix system. Thus, the fill material comprises, as its essential components, the desired drug and the masticatory substance. Other materials, such as paraffin, mineral oil, neutral oils, and the like may be added to the fill material in order to attain the desired consistency of the fill material for filling purposes, that is, for filling of the fill material into a gelatin capsule, preferably a soft elastic gelatin capsule, although two piece hard shell gelatin capsules may also be used. Not only is the flowability of the fill material important for filling purposes for soft gelatin capsules, but it is also important that the fill material provide the desired drug release profile following administration and swallowing of the encapsulated drug.

The masticatory substance useful as the gum matrix is generally a gum of the type listed in the Code of Federal Regulations, Title 21, Section 172.615. Suitable insoluble masticatory substances utilized in our method and product include various natural and synthetic masticatory substances or elastomers which may be used alone or in a variety of combinations. Such natural masticatory substances (coagulated or concentrated lattices) of vegetable origin are as follows: Chicle, Chiquibul, Crown gum, Gutta hang kang, Massaranduba balata (and the solvent-free resin extract of massaranduba balata), Massaranduba chocolate, Nispero, Rosidinha (rosadinha), Venezuelan chicle, Jelutong, Leche caspi (sorva), Pendare, Peruillo, Lec he de vaca, Niger gutta, Tunu (tuno), Chite, and Natural rubber (smoked sheet and latex Hevea brasiliensis solids). Suitable synthetic masticatory substances include: Butadiene-styrene rubber, isobutylene-isoprene copolymer (butyl rubber), silicone elastomers, paraffin, petroleum wax, petroleum wax synthetic, polyethylene (mol. wt. 2,000-21,000), polyisobutylene (mol. wt. 37,000), polyvinyl acetate (mol. wt. 2,000), and polyvinyl alcohol (not listed in Fed. Reg.)

As indicated previously, various inert paraffins or oils may be utilized, if needed, in connection with the gum in order to obtain the desired consistency. The desired consistency is particularly important when filling the fill material into an SEG capsule.

In preparing the fill material, in order to attain the desired flow characteristics, it is important for the masticatory substance to be molten, while being mixed with the drug so that the drug is dispersed substantially uniformly throughout the fill matrix. The dispersion of the medicament within the masticatory substance is accomplished in a variety of ways. All the ingredients of the fill material, including the drug and the masticatory substance as well as other materials, such as the oils or paraffins, may be mixed together, with heating, if necessary, until the desired consistency for filling and the desired dispersion of the drug throughout the fill material is attained. Alternatively, the masticatory substance may be heated to molten temperatures and then the medicament may be added; the molten masticatory substance and the medicament are then mixed in order to obtain the desired consistency for filling and until the desired consistency is attained. An important aspect of the method for manufacture is appropriate mixing in order to provide a substantially uniform dispersion of the medicament in the molten masticatory substance.

One preferred masticatory gum particularly useful as a gum matrix is a synthetic masticatory substance which is present in the fill in an amount of about 11%-28% by weight, a plasticizing material or softener present in a range of about 35%-57% by weight, a water insoluble adjuvant, such as calcium carbonate, which is present in an amount of about 40-50% by weight, and an antioxidant, such as butylated hydroxytoluene, which is present in very minor amounts, normally not more than 0.1% by weight. Typically, the gum base that is utilized as the masticatory substance has a softening end point of about 67°–76° C., an ash content of 46% plus or minus 2%, and a moisture content of 1% maximum.

In a preferred aspect of the present invention, the fill material is filled into a soft elastic gelatin shell which encloses the fill material, including the drug, which does not attack the walls of the seamless, one piece soft elastic gelatin capsule. The gelatin capsule shell is formulated in accordance with conventional techniques for masking filled, seamless, soft elastic gelatin capsules containing therapeutically effective unit dosage amounts of an active drug ingredient. In one conventional shell formulation, there is included about 30–53 parts by weight of gelatin, about 15–48 parts by weight of a plasticizer, such as glycerin or sorbitol, and about 16–40 parts by weight of water. Additionally, the gelatin shell may contain preservatives, such as mixed parabens, ordinarily methyl or propyl parabens in about a 4:1 ratio. The parabens may be incorporated in the shell formulation in minor proportions as compared to the total weight of the shell formulation. Conventional gelatin capsules utilize gelatin having a Bloom value of about 160–200 although this value may be varied over a wider range. In a conventional manner, the gelatin composition is mixed and melted under vacuum conditions. The capsules may be simultaneously formed and filled using conventional methods and apparatus such as disclosed, for example, in U.S. Pat. Nos. 1,970,396; 2,288,327; and 2,318,718. The gelatin capsules are formed into the desired shape and size so that they can be readily swallowed, usually with the aid of water.

Upon incorporation of the fill material, including the masticatory gum and the medicament, into the gelatin shell, since the capsule is soluble in water and in the gastrointestinal juices, upon swallowing, the gelatin shell rapidly dissolves in the stomach leaving the substantially insoluble fill material. Referring to FIG. 1, there is shown a cross sectional view of a typical capsule 10 made in accordance with our invention. The capsule 10 includes the gelatin shell 12 and the fill material 14 comprising the masticatory gum matrix that supports the medicament. Referring to FIG. 2, the fill material is shown upon dissolution of the gelatin shell in the stomach. Referring to FIG. 3, the fill material 14 is shown during early convolutions or movement imparted to the fill material as a result of the softening of the fill material by the body temperature, while in the gastric juices, and while under the influence of peristaltic motion within the stomach. Referring to FIG. 4, it is clearly seen that there is a new surface area exposure of the fill material 14 due to the convolutions imparted thereto by the influence of peristaltic movement. As the fill material 14 passes through the gastrointestinal tract including the stomach and small intestine towards the large intestine or colon, there are further convolutions imparted to the fill material 14 until the insoluble fill material is all that remains and substantially all the drug has been released. The insoluble fill material passes through the entire gastrointestinal tract to the lower intestine or colon until substantially all the drug is released from the matrix, and is ultimately excreted from the system.

Since the fill material is insoluble and non-toxic and because of the convolutions that are imparted to the fill material 14 over an extended period of time through peristaltic motion imparted thereto, during time in the gastrointestinal tract, such as 24 to 36 hours, the desired sustained release effect for the selected drug is attained. Data show that the masticatory gum matrix system remains a cohesive, semi-solid mass while under the action of normal gastrointestinal motility. For example, in in vivo testing, the cohesive masticatory gum matrix gum system controls the continuous release of an initial dosage, for example, three hundred milligrams of the drug theophylline, initially contained in a soft elastic gelatin capsule during passage through the gastrointestinal tract over a period of about 24 hours. In test, the bioavailability of the drug was determined by monitoring the human saliva theophylline concentration by high performance liquid chromatography. In in vitro studies there was no more than 20% of theophylline released in 900 milliliters of water at 37° C. in 7 hours as determined by the U.S.P. Paddle Method at 50 r.p.m. There was no less than 40 percent theophylline dissolved in 50 ml of water at 37° C. at 7 hours as measured by a rotating bottle method. The system's degree of sustained release action is apparent from testing which will be described in detail. Generally speaking, the continuous sustained release effect of the drug or other chemical from the cohesive, semi-solid masticatory gum matrix gum is not affected by pH changes of going from the stomach to the intestine.

The following examples set forth test results illustrating the advantages of the present invention. The following test results show the sustained release effects of the present invention utilizing a capsule composition comprising a soft elastic gelatin capsule containing a fill of 300 milligrams of theophylline (anhydrous). The formulation of the fill material was:

| | |
|---|---|
| Theophylline (anhydrous), USP | 300.000 (+ or − 10%) |
| Neutral Oil | 240.000 + or − 10%) |
| Masticatory Substance | 225.000 + or − 10% |
| Mineral Oil, USP | 50.000 + or − 10% |
| Paraffin, NF | 50.000 + or − 10% |

The shell formulation was as follows:

| | |
|---|---|
| Gelatin USP (type 195) | 217.859 (+ or − 10%) |
| Glycerin, USP | 132.318 (+ or − 10%) |
| Purified water, USP | 26.907 (+ or − 10%) |
| Methyparaben, NF | .864 (+ or − 10%) |
| Propylparaben | 0.216 (+ or − 10%) |

The theoretical capsule fill weight was 865 milligrams plus or minus 10%, the theoretical capsule fill volume was 12.44 minims plus or minus 10%, the die size (R. P. Scherer Corporation) was W/16 oval B, the die dimensions were a height of 0.46 inches plus or minus 10%, and a diameter of 0.70 inches plus or minus 10%, and the capsule was opaque white in color.

EXAMPLE 1

The purpose of the test was to determine the rate and extent of theophyllne absorption from the sustained release dosage formulation of the present invention as compared to an immediately released theophylline product following administration of a single dose. The capsules utilized were the 300 milligram sustained release theopyllne capsule as described above having a preferred fill material of the present invention. Test results were compared against Eloxophyllin ® an elixir manufactured by Berlex Laboratories.

Twenty normal and healthy non-smoking males were utilized for the experiment. The subjects met the following criteria of eligibility for participation in the experiment: (a) 19-35 years of age; (b) no more than plus or minus 15% from ideal weight for their height, as defined by Metropolitan Life Insurance Company Statistical Bulletin 40: 1, 1959, and a weight of greater than or equal to 125 lbs.; (c) no history of serious hepatic, renal, gastrointestinal or cardiovascular disease, alcohol or drug abuse, as evidenced by a medical history, physical examination and vital signs within 30 days prior to the start of the study; and (d) blood chemistry hematology and urinalysis were performed to eliminate potential subjects who did not have test values within normal ranges.

for each subject is also included. Twelve of eighteen subjects had AUC values for the capsule that fell within 70% of their AUC values for the elixir. The overall relative bioavailability, F%, determined over a 24 hour period was 94.5%.

Table II compares the values for peak times, $t_{max}$, and peak blood levels, $c_{max}$, obtained for the capsule and the elixir in each individual. The average $c_{max}$ for the sustained release product was 6.31 μg/ml. and the average $t_{max}$ was 4.39 hours. For the elixir, an average $c_{max}$ of 8.25 μg/ml was achieved and the average $t_{max}$ was 1.47 hours.

TABLE I

Comparison of AUC's for Human Subjects Receiving a Single Dose, 300 mg, of Elixir of Theophylline (Berlex Labs. Inc.) and Sustained Release Capsules of Theophylline (R.P. Scherer)

| Sample | Subject | | | | | | | | | Average |
|---|---|---|---|---|---|---|---|---|---|---|
| | 1 | 2 | 4 | 5 | 7 | 8 | 9 | 10 | 11 | |
| Sustained Release | 91.52 | 81.95 | 97.63 | 98.15 | 69.96 | 78.62 | 68.03 | 61.07 | 54.74 | 76.96 |
| Elixir | 94.37 | 79.23 | 58.58 | 82.13 | 95.89 | 90.56 | 67.69 | 91.52 | 91.28 | 83.47 |
| Bioavailability (F %) | 98 | 103 | 167 | 109 | 73 | 87 | 101 | 67 | 60 | 96.00 |

| Sample | Subject | | | | | | | | Average | Average of 18 Subjects |
|---|---|---|---|---|---|---|---|---|---|---|
| | 12 | 13 | 14 | 15 | 16 | 17 | 18 | 19 | 20 | |
| Sustained Release | 60.00 | 66.71 | 51.93 | 66.51 | 71.79 | 80.07 | 69.61 | 108.86 | 94.47 | 74.44 | 75.70 |
| Elixir | 58.37 | 100.72 | 78.04 | 80.36 | 98.72 | 90.88 | 89.46 | 70.57 | 75.61 | 82.53 | 83.00 |
| Bioavailability (F %) | 103 | 66 | 67 | 83 | 73 | 88 | 78 | 156 | 125 | 93.00 | 94.50 |

AUC determined over 24 hour period $$F\% = \frac{AUC\ g/ml \times hr.\ (Sustained\ Release)}{AUC\ g/ml \times hr.\ (Elixir)} \times 100$$

TABLE II

Comparison of the $t_{max}$ and $c_{max}$ for Theophylline in Human Subjects Receiving a Single Oral Dose, 300 mg, of Sustained Release ("S.R.") capsules (R. P. Scherer) and Elixir (Berlex Labs, Inc.)

| Subject | | 1 | 2 | 4 | 5 | 7 | 8 | 9 | 10 | 11 | Average |
|---|---|---|---|---|---|---|---|---|---|---|---|
| $t_{max}$ (hours) | Elixir | 3.0 | 3.0 | 1.0 | 1.0 | 1.0 | 1.0 | 3.0 | 0.5 | 0.5 | 1.56 |
| | S.R. | 3.0 | 5.0 | 5.0 | 7.0 | 6.0 | 6.0 | 2.0 | 4.0 | 5.0 | 4.78 |
| $c_{max}$ (g/ml) | Elixir | 7.47 | 9.04 | 7.25 | 7.96 | 7.99 | 8.18 | 7.18 | 10.88 | 10.00 | 8.44 |
| | S.R. | 8.40 | 7.78 | 7.33 | 7.71 | 5.68 | 5.34 | 7.44 | 5.32 | 4.90 | 6.66 |

| Subject | | 12 | 13 | 14 | 15 | 16 | 17 | 18 | 19 | 20 | Average | Average (18 Subjects) |
|---|---|---|---|---|---|---|---|---|---|---|---|---|
| $t_{max}$ (hours) | Elixir | 3.0 | 1.0 | 2.0 | 1.0 | 1.0 | 1.0 | 0.5 | 1.0 | 2.0 | 1.39 | 1.47 |
| | S.R. | 5.0 | 4.0 | 4.0 | 2.0 | 4.0 | 6.0 | 4.0 | 3.0 | 4.0 | 4.00 | 4.39 |
| $c_{max}$ (g/ml) | Elixir | 5.92 | 8.93 | 7.69 | 8.17 | 9.96 | 8.84 | 7.50 | 8.55 | 7.00 | 8.06 | 8.25 |
| | S.R. | 5.39 | 4.99 | 5.60 | 5.89 | 6.28 | 5.40 | 5.62 | 7.62 | 6.80 | 5.95 | 6.31 |

After an overnight fast, each subject was fitted with either a Cathelon IV (18G, 1¾ in.) I.V. catheter or a butterfly infusion set, each equipped with a Jelco intermittent injection cap as a heparin lock. A baseline blood sample was drawn within 15 minutes of each subject's scheduled dose time. A standard blood withdrawal procedure was employed. Each subject was then given a 300 mg dose of theophylline as either the sustained release capsule of the present invention or Elixophyllin ® at his scheduled dose time. Xanthine-free meals were served to the subjects during the course of the day. Plasma samples were drawn at the following time intervals after dosing: 0, 0.5, 1, 2, 3, 4, 5, 6, 8, 10, 12 and 24-hours. After the 12 hour blood draw was complete, the catheters were removed. The 24 hour samples were obtained using routine venipuncture techniques.

FIG. 6 is a graphic summary of the average plasma concentration of theophylline following a single oral dose of 300 mg of the sustained release capsule of the present invention and Elixophyllin ® elixir, 80 mg/15 ml (Lot No. W10835, Exp. 11/84). Table I summarizes the area under the curve ("AUC") of FIG. 6 data for both the sustained release capsule and the theophylline elixir. A comparison of individual bioavailability values

EXAMPLE II

The human subjects of Example I were utilized for the study detailed in this Example. Again, the purpose of the study was to compare the theophylline levels of a sustained release capsule containing the fill material made in accordance with the present invention, an intermediate release reference product, and a sustained release reference product following a multiple dosing regimen designed to achieve steady state plasma levels of theophylline.

The samples examined were the 300 mg sustained release capsule, of the present invention, discussed above, containing a fill of theophylline, Elixophyllin ® elixir, 80 mg/15 ml, manufactured by Berlex Laboratories as the intermediate release reference product, and sustained release tablets containing theophylline as manufactured by Key Pharmaceuticals, Inc., as a reference material.

The single dose study of Example I served as the pre-test dose evaluation for the multiple dose, steady state study. The subjects were instructed to avoid the use of any other medication, including non-prescription drugs, on a regular basis, from one week prior to the beginning of the study and throughout its 22-day duration. They were also instructed to exclude all xanthine-containing foods and beverages from 48 hours prior to the initiation of the study until after the study was completed. Fasting overnight was required between days 4 and 5, 12 and 13, and 20 and 21.

The subjects were divided into 3 groups which participated in three separate five-day treatment periods, one for each sample tested. The 22-day multiple dose study included a 4-day washout between each of the separate treatment periods. The sustained release capsule having the fill material of the present invention and the sustained release reference tablet were administered according to identical dosage schedules. A dose of 300 mg of the capsule or 300 mg of the tablet were administered in the morning and evening on the first through the fourth days and in the morning of the fifth day of the treatment period. A dose of 200 mg of the intermediate release reference elixir was administered in the morning only on the fifth day. A dose was also self administered by each patient at midnight of each day.

For the sustained release capsule and tablet, plasma samples were taken in the morning and evening of the fourth day of the treatment period and, on the fifth day, at 0, 0.5, 1, 2, 3, 4, 6, 8, 10, 12, 16 and 24 hours following the final dose of the treatment period. For the intermediate release elixir, plasma samples were taken, for each treatment period, in the morning and afternoon of the fourth day, and, on the fifth day, at 0, 0.5, 1, 2, 3, 4, 6, 8, 10, 12, 16 and 24 hours following the final dose of the treatment period.

The average plasma concentrations of theophylline in the 18 human subjects after 5 days of multiple dosing of the three samples are shown graphically in FIG. 7. A dose of 200 mg as the elixir (Berlex Lot No. W10836, Exp. 11/84) was administered every 8 hours and 300 mg as the sustained release capsules (Scherer Lot No. E11994), containing the fill material of the present invention, and 300 mg of the sustained release tablets (Key Lot No. 220031, Exp. 2/84) was administered every 12 hours to achieve the steady state theophylline levels. Subjects receiving the elixir exhibited highest levels within 2 hours and the lowest levels after 6 hours. Plasma levels for the sustained release capsules and the sustained release tablets were similar from 1 hour through 10 hours. The sustained release capsule produced higher levels through that time period and slightly lower at zero hours and 12 hours.

Tables III, IV and V present a comparison of the areas under the curves ("AUC") of FIG. 2 and relative bioavailabilities, F%, between samples for each individual over a 12 hour time period for the sustained release capsules and sustained release tablets and an 8 hour time period for the elixir. The AUC for the elixir reported was multiplied by 1.5 to normalize the data for the smaller dose. This is probably an over-estimate because it does not take into account the residual theophylline from previous dosing. The average F% for the sustained release capsules was greater than for the sustained release tablets. Both exhibited AUC's less than the elixir. Sixteen of the 18 subjects had AUC values for the sustained release capsules that fell within 79% of their AUC values for the elixir. Thirteen of the 18 subjects had AUC values for the sustained release tablet that fell within 76% of their AUC values for the elixir.

The overall bioavailability, F%, for the sustained release capsules was 88.58%, compared with 84.18% for the sustained release tablets. (Average data presented in Table V.) Tables VIa, VIb and VIc present a comparison of peak blood levels of theophylline, $c_{max}$, peak times, $t_{max}$, and average minimum blood levels of theophylline, $c_{min}$, values for the subjects by group. The combined average for each parameter is presented in Table VIa. The sustained release capsules had an average $c_{max}$ of 11.46 g/ml and an average $t_{max}$ of 4.42 hours, while the sustained release tablets had an average $c_{max}$ of 9.91 g/ml and an average $t_{max}$ of 3.56 hours. The elixir had an average $c_{max}$ of 13.75 g/ml and an average $t_{max}$ of 1.06 hours. The average $c_{min}$ value for the sustained release capsules was 6.62 g/ml compared to 7.67 g/ml for the sustained release tablets and 7.75 g/ml for the elixir.

As can be seen from the data in Tables VIa, VIb and VIc, a significant difference was observed between the AUC values for the elixir and both the sustained release capsules and sustained release tablets. There was no significant difference between the AUC values for the sustained release capsules and the sustained release tablets. The $c_{min}$ values for the elixir and the sustained release tablets were not significantly different from one another but both were significantly different from that of the sustained release capsules. The $t_{max}$ values for the sustained release capsules and the sustained release tablets were not significantly different from one another but were significantly different from the $t_{max}$ for the elixir. There was also a significant difference between the $c_{max}$ values of all 3 samples with the elixir having the highest value and the value of the sustained release capsules being higher than that of the sustained release tablets. No significant variation was seen between subject groups.

For the data reported in Examples I and II, the following procedure was used to obtain the data: The fresh plasma samples taken from the subjects were centrifuged and were then separated, labeled and frozen. The plasma samples for each subject were grouped as individual sample sets after each 24-hour sampling period. Prior to analysis, each set of samples was allowed to thaw at room temperature. The samples were then prepared for analysis by adding, to 0.5 ml of the plasma, 0.1 ml of a standard solution which consisted of 1 ml of aqueous solution containing 0.5 mg of -hydroxy ethyl theophylline (H-9006, Sigma Chem. Co.) added to 9 ml of 20% caffiene in acetonitrile. The sample-standard solution was then vortexed for 30 seconds in a Vortex Genie, allowed to stand for 30 minutes, and then centrifuged for 20 minutes at 10,000 r.p.m. in an Eppendorf Model No. 5412 centrifuge. The resulting plasma filtrate was removed for analysis and the precepitate was discarded. A 0.1 ml sample of the plasma filtrate was then injected into a Beckman High Performance Chromatograph, Model 110A, equipped with a Hewlett-Packard 3390A integrator-recorder. All theophylline concentrations were determined in duplicate using the theophylline peak curves from the integrator-recorder and a standard curve for theophylline.

Examples I and II demonstrate that the sustained release capsules having the fill material of the present invention provide therapeutic equivalence to thesustained release tablets without the dager of reaching toxic theophylline levels when utilizing a 12 hour dosage interval.

TABLE III

Comparison of AUC's for Subjects at the End of Five Days of Multiple Dosing of Theophylline Products. Each Subject Received 300 mg Every 12 Hours of Sustained Release Capsules (S.R.I) (R.P. Scherer), 300 mg Every 12 Hours of Sustained Release Tablets (S.R.II) (Key Pharmaceuticals, Inc.) and 200 mg Every 8 Hours of the Elixir (Berlex Laboratories, Inc.) on Alternate Weeks During the Triple Crossover Phase of the Study.

| Sample | Subject | | | | | | |
|---|---|---|---|---|---|---|---|
| | 2 | 4 | 6 | 7 | 8 | 21 | Average |
| AUC (S.R.I) (Scherer) | 112.50 | 107.91 | 114.48 | 111.62 | 113.45 | 100.02 | 110.00 |
| AUC (S.R.II) (Key) | 80.05 | 118.18 | 136.99 | 99.03 | 115.07 | 99.85 | 108.20 |
| AUC (Elixir) (Berlex) | 124.08 | 121.86 | 118.85 | 104.94 | 133.22 | 145.08 | 124.67 |
| Bioavailability: F % $\frac{\text{AUC-S.R.I}}{\text{AUC-Elix.}} \times 100$ | 90.66 | 88.55 | 96.32 | 106.37 | 85.16 | 68.94 | 89.33 |
| F % $\frac{\text{AUC-S.R.II}}{\text{AUC-Elix.}} \times 100$ | 64.51 | 96.98 | 115.92 | 94.37 | 86.38 | 68.82 | 87.83 |
| F % $\frac{\text{AUC-S.R.I}}{\text{AUC-S.R.II}} \times 100$ | 140.53 | 91.31 | 83.57 | 112.71 | 98.59 | 100.17 | 104.48 |

AUC, g/ml × hr. was determined over a 12 hour period beginning on the morning of the 5th dosing day for the Sustained Release Capsules and Sustained Release Tablets. The AUC for Elixir of Theophylline was determined over an 8 hour period beginning on the morning of the 5th dosing day and the calculated AUC was multiplied by a factor of 1.5 to normalize the data for a smaller dose of 200 mg.

TABLE IV

Comparison of AUC's for Subjects at the End of Five Days of Multiple Dosing of Theophylline Products. Each Subject Received 300 mg Every 12 Hours of Sustained Release Capsules (S.R.I) (R.P. Scherer), 300 mg Every 12 Hours of Sustained Released Tablets (S.R.II) (Key Pharmaceuticals, Inc.) and 200 mg Every 8 Hours of the Elixir (Berlex Laboratories, Inc.) on Alternate Weeks During the Triple Crossover Phase of the Study.

| Sample | Subject | | | | | | |
|---|---|---|---|---|---|---|---|
| | 9 | 10 | 11 | 12 | 13 | 14 | Average |
| AUC (S.R.I) (Scherer) | 114.64 | 102.28 | 110.50 | 62.95 | 140.70 | 132.25 | 110.55 |
| AUC (S.R.II) (Key) | 116.17 | 88.29 | 80.87 | 75.08 | 121.17 | 84.87 | 94.41 |
| AUC (Elixir) (Berlex) | 117.73 | 116.21 | 100.77 | 79.09 | 142.30 | 148.78 | 117.48 |
| F % $\frac{\text{AUC-S.R.I}}{\text{AUC-Elix.}} \times 100$ | 97.38 | 88.01 | 109.63 | 79.59 | 98.88 | 88.89 | 93.06 |
| F % $\frac{\text{AUC-S.R.II}}{\text{AUC-Elix.}} \times 100$ | 98.67 | 75.97 | 80.25 | 94.93 | 85.15 | 57.04 | 82.00 |
| F % $\frac{\text{AUC-S.R.I}}{\text{AUC-S.R.II}} \times 100$ | 98.68 | 115.85 | 136.64 | 83.84 | 116.12 | 155.83 | 117.83 |

AUC, g/ml × hr. was determined over a 12 hour period beginning on the morning of the 5th dosing day for the Sustained Release Capsules and Sustained Release Tablets. The AUC for Elixir of Theophylline was determined over an 8 hour period beginning on the morning of the 5th dosing day and the calculated AUC was multiplied by a factor of 1.5 to normalize the data for a smaller dose of 200 mg.

TABLE V

Comparison of AUC's for Subjects at the End of Five Days of Multiple Dosing of Theophylline Products. Each Subject Received 300 mg Every 12 Hours of Sustained Release Capsules (S.R.I) (R.P. Scherer), 300 mg. Every 12 Hours of Sustained Release Tablets (S.R.II) (Key Pharmaceuticals, Inc.) and 200 mg Every 8 Hours of the Elixir (Berlex Laboratories, Inc.) on Alternate Weeks During the Triple Crossover Phase (Phase II) of the Study.

| Sample | Subject | | | | | | Average | Average of 18 Subjects |
|---|---|---|---|---|---|---|---|---|
| | 15 | 16 | 17 | 18 | 19 | 20 | | |
| AUC (S.R.I) (Scherer) | 70.74 | 143.27 | 118.84 | 111.99 | 101.89 | 104.89 | 108.60 | 109.72 |
| AUC (S.R.II) (Key) | 83.18 | 146.83 | 127.35 | 118.52 | 94.65 | 82.11 | 108.78 | 103.79 |
| AUC (Elixir) (Berlex) | 123.60 | 150.66 | 132.32 | 128.10 | 119.98 | 128.53 | 130.53 | 124.23 |
| $F\% \frac{AUC\ S.R.I}{AUC\text{-}Elix.} \times 100$ | 57.23 | 95.09 | 89.81 | 87.42 | 84.92 | 81.61 | 82.68 | 88.58 |
| $F\% \frac{AUC\text{-}S.R.II}{AUC\text{-}Elix.} \times 100$ | 67.30 | 97.46 | 96.24 | 92.52 | 78.89 | 63.88 | 81.05 | 84.18 |
| $F\% \frac{AUC\text{-}S.R.I}{AUC\text{-}S.R.II} \times 100$ | 85.04 | 97.56 | 93.35 | 94.49 | 107.65 | 127.74 | 100.97 | 107.76 |

AUC, g/ml × hr. was determined over a 12 hour period beginning on the morning of the 5th dosing day for the Sustained Released Capsules and Sustained Release Tablets. The AUC for Elixir of Theophylline was determined over an 8 hour period beginning on the morning of the 5th dosing day and the calculated AUC was multiplied by a factor of 1.5 to normalize the data for a smaller dose of 200 mg.

TABLE VI

A Comparison of $C_{max}$, $t_{max}$, and Average $C_{min}$'s for Subjects Receiving Theophylline Products. Each Subject Received Oral Doses of 300 mg of Sustained Release Capsules (S.R.I) (R. P. Scherer), 300 mg of Sustained Release Tablets (S.R.II) (Key Pharmaceuticals) Every 12 Hours for 5 days, and 200 mg of Elixir (Berlex Labs) Every 8 Hours for 5 Days on Alternate Weeks During the Triple Crossover Phase (Phase II) of the Study.

| | Subject | Sample | | | | | | Average N = 6 | Combined Ave. N = 18 |
|---|---|---|---|---|---|---|---|---|---|
| | | 2 | 4 | 6 | 7 | 8 | 21 | | |
| $C_{max}$ (g/ml) | S.R.I (Scherer) | 12.38 | 10.39 | 10.72 | 13.03 | 11.32 | 10.78 | 11.43 | 11.46 |
| | S.R. II (Key) | 8.13 | 11.93 | 12.44 | 9.61 | 10.72 | 9.03 | 10.31 | 9.91 |
| | Elixir (Berlex) | 14.42 | 13.78 | 13.00 | 11.11 | 14.00 | 14.93 | 13.54 | 13.75 |
| $t_{max}$ (hours) | S.R.I (Scherer) | 4.0 | 5.0 | 8.0 | 2.0 | 6.0 | 5.0 | 5.0 | 4.42 |
| | S.R.II (Key) | 6.0 | 1.0 | 1.0 | 5.0 | 2.0 | 6.0 | 3.5 | 3.56 |
| | Elixir (Berlex) | 0.5 | 2.0 | 1.0 | 1.0 | 1.0 | 2.0 | 1.25 | 1.06 |
| $C_{min}^*$ (g/ml) | S.R.I (Scherer) | 5.35 | 7.81 | 7.86 | 6.34 | 6.91 | 6.96 | 6.87 | 6.62 |
| | S.R.II (Key) | 4.89 | 8.76 | 10.42 | 7.80 | 9.21 | 7.52 | 8.10 | 7.67 |
| | Elixir (Berlex) | 7.89 | 6.17 | 6.70 | 8.00 | 7.93 | 9.80 | 7.75 | 7.75 |

| | | 9 | 10 | 11 | 12 | 13 | 14 | Average N = 6 | |
|---|---|---|---|---|---|---|---|---|---|
| $C_{max}$ (g/ml) | S.R.I (Scherer) | 11.39 | 11.81 | 10.25 | 7.67 | 14.07 | 14.25 | 11.57 | |
| | S.R.II (Key) | 8.20 | 13.38 | 13.00 | 10.94 | 9.02 | 8.42 | 10.49 | |
| | Elixir (Berlex) | 13.60 | 13.88 | 12.07 | 9.12 | 15.98 | 15.53 | 13.36 | |
| $t_{max}$ (hours) | S.R.I (Scherer) | 6.0 | 5.0 | 8.0 | 5.0 | 3.0 | 3.0 | 5.00 | |
| | S.R.II (Key) | 4.0 | 6.0 | 8.0 | 3.0 | 0.0 | 2.0 | 3.83 | |
| | Elixir (Berlex) | 1.0 | 1.0 | 0.5 | 2.0 | 0.5 | 1.0 | 1.00 | |
| $C_{min}^*$ (g/ml) | S.R.I (Scherer) | 5.93 | 5.30 | 6.93 | 3.52 | 8.78 | 7.19 | 6.28 | |
| | S.R.II (Key) | 6.08 | 9.23 | 9.75 | 8.34 | 7.32 | 7.29 | 8.00 | |

TABLE VI-continued

A Comparison of $C_{max}$, $t_{max}$, and Average $C_{min}$'s for Subjects Receiving Theophylline Products. Each Subject Received Oral Doses of 300 mg of Sustained Release Capsules (S.R.I) (R. P. Scherer), 300 mg of Sustained Release Tablets (S.R.II) (Key Pharmaceuticals) Every 12 Hours for 5 days, and 200 mg of Elixir (Berlex Labs) Every 8 Hours for 5 Days on Alternate Weeks During the Triple Crossover Phase (Phase II) of the Study.

|  |  |  |  |  |  |  |  |
|---|---|---|---|---|---|---|---|
|  | Elixir (Berlex) | 6.65 | 7.15 | 5.84 | 3.92 | 9.86 | 9.28 | 7.12 |

|  |  | 15 | 16 | 17 | 18 | 19 | 20 | Average N = 6 |
|---|---|---|---|---|---|---|---|---|
| $C_{max}$ (g/ml) | S.R.I (Scherer) | 6.50 | 15.21 | 11.60 | 11.96 | 12.28 | 10.65 | 11.37 |
|  | S.R.II (Key) | 10.98 | 8.10 | 7.62 | 7.20 | 11.62 | 8.05 | 8.93 |
|  | Elixir (Berlex) | 14.17 | 15.20 | 13.65 | 12.99 | 14.45 | 15.57 | 14.34 |
| $t_{max}$ (hours) | S.R.I (Scherer) | 6.0 | 0.5 | 3.0 | 4.0 | 4.0 | 2.0 | 3.25 |
|  | S.R.II (Key) | 2.0 | 3.0 | 6.0 | 1.0 | 4.0 | 4.0 | 3.33 |
|  | Elixir (Berlex) | 0.5 | 1.0 | 2.0 | 1.0 | 0.5 | 0.5 | 0.92 |
| $C^*_{min}$ (g/ml) | S.R.I (Scherer) | 4.67 | 7.85 | 8.02 | 7.77 | 6.43 | 5.50 | 6.71 |
|  | S.R.II (Key) | 8.37 | 7.42 | 4.62 | 5.36 | 8.67 | 7.18 | 6.94 |
|  | Elixir (Berlex) | 7.55 | 9.27 | 10.25 | 6.85 | 7.99 | 8.42 | 8.38 |

*The average $C_{min}$ reported for the sustained release capsules and sustained release tablets represent an average of 4 values for each subject taken at 4 days, 4½ days, 5 days (0-time) and 5¼ days (12 hour-time). For the elixir, the $C_{min}$'s reported represent 4 values taken at 4 days, 4⅓ days, 5 days (0-time) and 5⅓ days (8 hour-time).

EXAMPLE III

A bioequivalency study was performed comparing a 100 mg sustained release capsule, made in accorance with the invention, to a commercially available sustained action theophylline tablet (THEODUR). The soft capsules were made in accordance with the formulaion of Example IV. The results are set forth below:

Study on Bioequivalency of Theophylline SR (Sustained Release) 100 mg Capsule (Crossover Study with Sustained Action Theophylline 100 mg Tablet)

TEST 1
Plasma Concentration in Human Subjects

| Sampling Time | No. 1 | No. 2 | No. 3 | No. 4 |
|---|---|---|---|---|
| 0.5 hr. | 0.36 mcg/ml | 0.20 mcg/ml | 0.43 mcg/ml | 0.55 mcg/ml |
| 1.0 hr | 0.65 mcg/ml | 0.34 mcg/ml | 0.80 mcg/ml | 0.82 mcg/ml |
| 2.0 hr | 0.79 mcg/ml | 0.50 mcg/ml | 1.52 mcg/ml | 1.05 mcg/ml |
| 4.0 hr | 1.54 mcg/ml | 0.56 mcg/ml | 2.92 mcg/ml | 1.10 mcg/ml |
| 6.0 hr | 1.81 mcg/ml | 1.30 mcg/ml | 1.94 mcg/ml | 1.11 mcg/ml |
| 8.0 hr | 1.69 mcg/ml | 1.21 mcg/ml | 1.85 mcg/ml | 1.13 mcg/ml |
| 12.0 hr | 1.21 mcg/ml | 0.83 mcg/ml | 1.32 mcg/ml | 1.20 mcg/ml |
| 24.0 hr | 0.60 mcg/ml | 0.18 mcg/ml | 0.47 mcg/ml | 0.66 mcg/ml |

Note:
No. 1, 2 - Theophylline SR 100 mg capsule
No. 3, 4 - Theophylline 100 mg tablet

TEST 2
Plasma Concentration in Human Subjects

| Sampling Time | No. 1 | No. 2 | No. 3 | No. 4 |
|---|---|---|---|---|
| 0.5 hr | 0.73 mcg/ml | 0.55 mcg/ml | 0.13 mcg/ml | 0.65 mcg/ml |
| 1.0 hr | 1.03 mcg/ml | 0.80 mcg/ml | 1.99 mcg/ml | 0.97 mcg/ml |
| 2.0 hr | 1.42 mcg/ml | 1.01 mcg/ml | 3.11 mcg/ml | 1.26 mcg/ml |
| 4.0 hr | 1.63 mcg/ml | 1.04 mcg/ml | 1.76 mcg/ml | 1.48 mcg/ml |
| 6.0 hr | 1.98 mcg/ml | 1.61 mcg/ml | 1.99 mcg/ml | 2.26 mcg/ml |
| 8.0 hr | 1.95 mcg/ml | 1.68 mcg/ml | 1.97 mcg/ml | 2.71 mcg/ml |
| 12.0 hr | 1.17 mcg/ml | 1.29 mcg/ml | 1.28 mcg/ml | 1.80 mcg/ml |
| 24.0 hr | 0.44 mcg/ml | 0.38 mcg/ml | 0.68 mcg/ml | 0.68 mcg/ml |

Note:
No. 1, 2 - Theophylline 100 mg tablet
No. 3, 4 - Theophylline SR 100 mg capsule

TEST 3
Plasma Concentration in Human Subjects

| TheoDur tablet | | | Theophylline SR capsule | | |
|---|---|---|---|---|---|
| T max. | C max. | AUC | T max. | C max. | AUC |

-continued

Study on Bioequivalency of Theophylline SR (Sustained Release) 100 mg Capsule (Crossover Study with Sustained Action Theophylline 100 mg Tablet)

| | | | | | | |
|---|---|---|---|---|---|---|
| No. 1 | 6.0 | 1.98 | 28.34 | 6.0 | 1.81 | 26.90 |
| No. 2 | 8.0 | 1.68 | 25.33 | 6.0 | 1.30 | 16.18 |
| No. 3 | 4.0 | 2.92 | 31.74 | 2.0 | 3.11 | 33.95 |
| No. 4 | 12.0 | 1.20 | 23.84 | 8.0 | 2.71 | 37.03 |
| Average ± SD | 7.5 ± 3.42 | 1.95 ± 0.73 | 27.31 ± 3.48 | 5.5 ± 2.52 | 2.23 ± 0.83 | 28.52 ± 9.25 |

T max.: hr.
C max.: mcg/ml
AUC: mcg/ml · hr

There were no statistically significat differences in C max. T max. and AUC between the two preparations.

EXAMPLE IV

Dissolution studies were performed on soft gelatin capsules containing a fill material made in accorance with the invention and containing theophylline, as set forth below. The shell formulation was conventional and was composed of gelatin and glycerin, in major proportion, water, and minor proportions of methyl and propyl parabens.

| Fill Ingredients | mg/Capsule |
|---|---|
| Theophylline (Bronchodilator) | 100.0 |
| Chewing Gum Base | 78.0 |
| Paraffin | 8.4 |
| Mineral Oil | 16.7 |
| Neutral Oil | 82.9 |

| DISSOLUTION RATE (N = 6) | | |
|---|---|---|
| TIME, hr | MEAN (mg) ± S.D. | % DISSOLVED |
| 1 | 20.0 ± 8 | 20.9 |
| 2 | 26.8 ± 14 | 27.9 |
| 3 | 35.5 ± 19 | 37.0 |
| 4 | 40.9 ± 21 | 42.6 |

EXAMPLE V

Dissolution studies were performed on soft gelatin capsules containing a fill material made in accordance with the invention and containing pseudoephedrine Hcl as set forth below. The shell formulation was conventional and was composed of gelatin and glycerin, in major proportion, water, and minor proportions of methyl and propyl parabens.

| Fill Ingredients | mg/Capsule |
|---|---|
| Pseudoephyedrine HCl (Decongestant) | 120.0 |
| Chewing Gum Base | 99.0 |
| Mineral Oil | 30.0 |
| Neutral Oil | 96.0 |

| DISSOLUTION RATE (N = 4) | | |
|---|---|---|
| TIME, hr | MEAN (mg) + S.D. | % DISSOLVED |
| 0.5 | 34.8 + 9.6 | 29 |
| 1.0 | 60.0 + 10.8 | 50 |
| 2.0 | 90.0 + 18.0 | 75 |
| 3.0 | 114.0 + 4.8 | 95 |
| 4.0 | 112.8 + 6.0 | 94 |
| 5.0 | 112.8 + 2.4 | 94 |

EXAMPLE VI

Dissolution studies were performed on soft gelatin capsules containing a fill material made in accordance with the invention and containing Indomethacin as set forth below. The shell formulation was conventional and was composed of gelatin and glycerin, in major proportion, water, and minor proportions of methyl and propyl parabens.

| Fill Ingredients | mg/Capsule |
|---|---|
| Indomethacin (analgesic, Antipyretic, non-steroidal Anti-inflammatory) | 75 |
| Chewing Gum Base | 40 |
| Synthetic Cocoa Butter | 110 |
| Purified Stearic Acid | 15 |
| Lecithin | 2 |

| DISSOLUTION RATE | |
|---|---|
| TIME, hr | % RELEASED |
| 1.0 | 3% |
| 2.0 | 9.5% |
| 3.0 | 17.5% |
| 5.0 | 32.0% |
| 7.0 | 45.0% |
| 8.5 | 63.0% |
| 24.0 | 80.0% |

EXAMPLE VII

Dissolution studies were performed on soft gelatin capsules containing a fill material made in accordance with the invention and containing Propranolol HCl as set forth below. The shell formulation was conventional and was composed of gelatin and glycerin, in major proportion, water, and minor proportions of methyl and propyl parabens.

| Fill Ingredients | mg/Capsule |
|---|---|
| Propranolol HCl (Cardiovascular/Antihypertensive Drug) | 120 |
| Chewing Gum Base | 210 |
| Wecobee M** | 200 |
| Purified Stearic Acid | 70 |
| Neutral Oil | 30 |
| | 630 |

| DISSOLUTION (N = 6) | | |
|---|---|---|
| TIME, hr | MEAN (mg) + S.D. | % DISSOLVED |
| 1 | 5.43  0.44 | 4.5 |
| 2 | 7.99  0.80 | 6.7 |
| 3 | 11.52  1.81 | 9.6 |
| 5 | 16.45  3.33 | 13.7 |
| 8 | 23.40  3.77 | 19.5 |
| 16 | 33.08  2.71 | 27.6 |
| 20 | 35.83  3.13 | 29.9 |
| 24 | 43.98  3.36 | 36.7 |

**Triglycerides derived from edible vegetable oils

EXAMPLE VIII

Dissolution studies were performed on soft gelatin capsules containing a fill material made in accorance with the invention and containing Dimenhydrinate as set forth below. The shell formulation was conventional and was composed of gelatin and glycerin, in major proportion, water, and minor proportions of methyl and propyl parabens.

| Filled Ingredients | mg/Capsule |
|---|---|
| Dimenhydrinate (antinausea/antimotion sickness drug) | 75 |
| Chewing Gum Base | 225 |
| Paraffin | 60 |
| Mineral Oil, Heavy | 50 |
| Neutral Oil | 240 |
| Lactose | 200 |

| | DISSOLUTION (N = 9) | |
|---|---|---|
| TIME, hr | MEAN (mg) + S.D. | % DISSOLVED |
| 1 | 13.6      1.6 | 18.1 |
| 2 | 22.4      2.6 | 29.8 |
| 3 | 28.9      5.6 | 38.5 |
| 4 | 36.2      7.1 | 48.2 |
| 5 | 42.2      7.1 | 56.3 |
| 6 | 48.8      9.1 | 65.1 |
| 7 | 52.7      8.9 | 70.2 |
| 8 | 56.0      9.1 | 74.7 |

While in the foregoing there has been provided a detailed description of preferred embodiments of the present invention, it is to be understood that all equivalents obvious to those having skill in the art are to be included within the scope of the invention as claimed.

We claim:

1. A filled, gelatin capsule comprising in combination, a shell formed from gelatin, a fill material contained within said shell, said shell being sized and shaped to be readily swallowable, said fill material comprising a masticatory substance and a medicament dispersed throughout said substance, said medicament being of a type that is desirably and effectively gradually released for absorption by the body over an extended period of time, said substance defining a cohesive matrix for said medicament, said gelatin shell being rapidly dissolved in said gastrointestinal juices, said masticatory substance matrix being substantially insoluble in the presence of gastrointestinal juices, said matrix being of a type that is capable of being subjected to substantially continuous random motion while in said juices while at body temperature and while under the influence of peristaltic movement in the gastrointestinal tract for substantially varying the exposed surface area of said fill, and said medicament being gradually released over an extended period as said exposed surface area is varied for ultimate absorption of said medicament by the body.

2. The capsule of claim 1 wherein said gelatin shell is a one-piece, soft elastic gelatin capsule formed from gelatin, water and a plasticizer.

3. The capsule of claim 1 wherein said medicament is selected from the group consisting of antihistamines, sedatives, tranquilizers, cardiovascular drugs, respiratory drugs, sympathomimetic drugs, diuretic drugs, analgesics and antipyretics, antimotion sickness and antinauseants, and electrolytes and hematinics.

4. The capsule of claim 1 wherein said medicament is theophylline.

5. The capsule of claim 3 wherein said medicament is enclosed by an enteric coating.

6. The capsule of claim 1 wherein said fill material includes gum which comprises an insoluble, cohesive, masticatory substance.

7. The capsule of claim 6 wherein said fill material further includes paraffin, mineral oil, or neutral oil.

8. The capsule of claim 6 wherein the insoluble cohesive masticatory substance is a natural masticatory substances selected from the group consisting of Chicle, Chiquibul, Crown gum, Gutta hang kang, Massaranduba balata (and the solvent-free resin extract of Massaranduba balata), Massaranduba chocolate, Nispero, Rosidinha (rosadinha), Venezuelan chicle, Jelutong, Leche caspi (sorva), Pendare, Perillo, Leche de vaca, Niger gutta, Tunu (tuno), Chite, and Natural Rubber smoked sheet and latex Hevea brasiliensis solids).

9. The capsule of claim 6 wherein the masticatory substance is a synthetic masticatory substance selected from the group which consists of Butadiene-styrene rubber, isobutylene-isoprene copolymer (butyl rubber), silicone elastomers, paraffin, petroleum wax, petroleum wax synthetic, polyethylene (mol. wt. 2,000–21,000), polyisobutylene (mol. wt. 37,000), polyvinyl acetate (mol. wt. 2,000), and polyvinyl alcohol.

10. The capsule of claim 1 wherein said fill material comprises masticatory substance present in an amount of 11%–28% by weight, a plasticizing material present in an amount of about 35%–57% by weight, a water insoluble adjuvant present in an amount of about 40–50% by weight, and a minor amount of an antioxidant, said masticatory substance having a softening end point of about 67°–76° C., an ash content of 46%, plus or minus 2%, and a maximum moisture content of about 1%.

11. The capsule of claim 1 wherein said medicament nis pseudoephedrine.

12. The capsule of claim 1 wherein said medicament is indomethacin.

13. The capsule of claim 1 wherein said medicament is propranolol.

14. The capsule of claim 1 wherein said medicament is dimenhydrinate.

15. A method for gradually releasing a medicament for absorption by the body through the gastrointestinal system, said method comprising the steps of preparing a fill material of a masticatory substance and a medicament and said medicament being dispersed throughout said masticatory substance, said medicament being of the type that is desirably and effectively released for absorption from the gastrointestinal tract over an extended period of time, forming a supporting cohesive matrix for said medicament from said masticatory substance, said masticatory substance being substantially insoluble in gastrointestinal juices, forming a shell of gelatin around said fill material to form a filled capsule, said capsule being sized and shaped to be readily swallowable, orally administering said capsule, dissolving said gelatin shell after swallowing with said juices, subjecting said fill material with said medicament therein to substantially constant random motion while in said juices while at body temperatures and while under the influence of peristaltic movements in the gastrointestinal tract for continuously varying the surface area of said fill material, and gradually releasing said medicament from said exposed surface area over an extended period of time for absorption by the body.

16. The method of claim 15 wherein said gelatin shell is a one-piece, soft elastic gelatin capsule formed from gelatin, water and a plasticizer.

17. The method of claim 15 wherein said medicament is selected from the group consisting of antihistamines, sedatives, tranquilizers, cardiovascular drugs, respiratory drugs, sympathomimetic drugs, diuretic drugs, analgesics and antipyretics, antimotion sickness and antinauseants, and electrolytes and hematinics.

18. The method of claim 15 wherein said medicament is theophylline.

19. The method of claim 17 including the step of enteric coating said medicament.

20. The method of claim 15 wherein said masticatory substance includes an insoluble, cohesive, gum.

21. The method of claim 20 wherein said fill material further includes paraffin, mineral oil, or neutral oil.

22. The method of claim 15 wherein said masticatory substance is a natural masticatory substance selected from the group of Chicle, Chiquibul, Crown gum, Gutta hang kang, Massaranduba balata (and the solvent-free resin extract of Massaranduba balata), Massaranduba chocolate, Nispero, Rosidinha (rosadinha), Venezuelan chicle, Jelutong, Leche caspi (sorva), Pendare, Perillo, Leche de vaca, Niger gutta, Tunu (tuno), Chite, and Natural rubber (smoked sheet and latex Hevea brasiliensis solids).

23. The method of claim 15 wherein said masticatory gum substance is a synthetic masticatory substance selected from the group consisting of butadienestyrene rubber, isobutylene-isoprene copolymer (butyl rubber), silicone elastomers, paraffin, petroleum wax, petroleum wax synthetic, polyethylene (mol. wt. 2,000–21,000), polyisobutylene (mol. wt. 37,000), polyvinyl acetate (mol. wt. 2,000), and polyvinyl alcohol.

24. The method of claim 15 wherein said gum comprises a synthetic masticatory substance present in an amount of 11%–28% by weight, a plasticizing material or softener present in a range of about 35%–57% by weight, about 40%–50% by weight of a water insoluble adjuvant, and a minor amount of an antioxidant, said masticatory substance having a softening end point of about 67°–76° C., an ash content of 46% plus or minus about 2%, and a maximum moisture content of about 1%.

25. The method of claim 15 wherein said medicament is pseudoephedrine.

26. The method of claim 15 wherein said medicament is indomethacin.

27. The method of claim 15 wherein said medicament is propranolol.

28. The method of claim 15 wherein said medicament is dimenhydrinate.

29. An orally administered, sustained release dosage form comprising a filled dosage form comprising in combination, a shell, a fill material contained within said shell, said shell being sized and shaped to be readily swallowable, said fill material comprising a masticatory substance and a medicament dispersed throughout said subtance, said medicament being of a type that is desirably and effectively gradually released for absorption by the body over an extended period of time, said substance defining a cohesive matrix for said medicament, said shell being rapidly dissolved in said gastrointestinal juices, said masticatory substance matrix being substantially insoluble in the presence of gastrointestinal juices, said matrix being of a type that is capable of being subjected to substantially continuous random motion while in said juices while at body temperature and while under the influence of peristaltic movement in the gastrointestinal tract for substantially varying the exposed surface area of said fill, and said medicament being gradually released over an extended period as said exposed surface area is varied for ultimate absorption of said medicament by the body.

30. The capsule of claim 29 wherein said medicament is selected from the group consisting of antihistamines, sedatives, tranquilizers, cardiovascular drugs, respiratory drugs, sympathomimetic drugs, diuretic drugs, analgesics and antipyretics, antimotion sickness and antinauseants, and electrolytes and hematinics.

31. The capsule of claim 29 wherein said medicament is theophylline.

32. The capsule of claim 29 wherein said fill material includes gum which comprises an insoluble cohesive masticatory substance.

33. The capsule of claim 32 wherein the insoluble cohesive masticatory substance selected from the group consisting of Chicle, Chiquibul, Crown gum, Gutta hang kang, Massaranduba balata (and the solvent-free resin extract of Massaranduba balata), Massaranduba chocolate, Nispero, Rosidinha (rosadinha), Venezuelan chicle, Jelutong, Leche caspi (sorva), Pendare, Perillo, Leche de vaca, Niger gutta, Tunu (tuno), Chite, and natural Rubber smoked sheet and latex Hevea brasiliensis solids).

34. The capsule of claim 32 wherein the masticatory substance is a synthetic masticatory substance selected from the group which consists of Butadiene-styrene rubber, isobutylene-isoprene copolymer (butyl rubber), silicone elastomers, paraffin, petroleum wax, petroleum wax synthetic, polyethylene (mol. wt. 2,000–21,000), polyisobutylene (mol. wt. 37,000), polyvinyl acetate (mol. wt. 2,000), and polyvinyl alcohol.

35. The capsule of claim 29 wherein said fill material comprises masticatory substance present in an amount of 11%–28% by weight, a plasticizing material present in an amount of about 35%–57% by weight, a water insoluble adjuvant present in an amount of about 40%–50% by weight, and a minor amount of an antioxidant, said masticatory substance having a softening end point of about 67°–76° C., an ash content of 46%, plus or minus 2%, and a maximum moisture content of about 1%.

36. The capsule of claim 29 wherein said medicament is pseudoephedrine.

37. The capsule of claim 29 wherein the medicament is indomethacin.

38. The capsule of claim 29 wherein the medicament is propranolol.

39. The capsule of claim 29 wherein the medicament is dimenhydrinate.

40. A method for gradually releasing a medicament for absorption by the body through the gastrointestinal system, said method comprising the steps of preparing a fill material of a masticatory substance and a medicament and said medicament being disposed throughout said masticatory substance, said medicament being of the typr that is desirably and effectively released for absorption from the gastrointestinal tract over an extended period of time, forming a supporting cohesive matrix for said medicament from said masticatory substance, said masticatory substance being substantially insoluble in gastrointestinal juices, forming a shell around said fill material to form a fluid dosage form, said dosage form being sized and shaped to be readily swallowable, orally administering said dosage form, dissolving said shell, after swallowing, with said juices, subjecting said fill material with said medicament therein to substantially constant random motion while in said juices while at body temperatures and while under the influence of peristaltic movements in the gastrointestinal tract for continuously varying the surface area of said fill material, and gradually releasing said medicament from said exposed surface area over an extended period of time for absorption by the body.

41. The method of claim 40 wherein said medicament is selected from the group consisting of antihistamines, sedatives, tranquilizers, cardiovascular drugs, respiratory drugs, suympathomimetic drugs, diuretic drugs, analgesics and antipyretics, antimotion sickness and antinauseants, and electrolytes and hematinics.

42. The method of claim 40 wherein said medicament is theophylline.

43. The method of claim 40 wherein said masticatory substance is a natural masticatory substance selected from the group of Chicle, Chiquibul, Crown gum, Gutta hang kang, Massaranduba balata (and the solvent-free resin extract of Massaranduba balata), Massaranduba chocolate, Nispero, Rosidinha (rosadinha), Venezuelan chicle, Jelutong, Leche caspi (sorva), Pendare, Perillo, Leche de vaca, Niger gutta, Tunu (tuno), Chite, and Natural Rubber smoked sheet and latex Hevea brasiliensis solids).

44. The method of claim 40 wherein said masticatory gum substance is a synthetic masticatory substance selected from the group consisting of Butadienestyrene rubber, isobutylene-isoprene copolymer (butyl rubber), silicone elastomers, paraffin, petroleum wax, petroleum wax synthetic, polyethyelen (mol. wt. 2,000-21,000), polyisobutylene (mol. wt. 37,000), polyvinyl acetate (mol. wt. 2,000), and polyvinyl alcohol.

45. The method of claim 40 wherein said masticatory substance comprises a synthetic masticatory substance present in an amount of 11%-28% by weight, a plasticizing material or softener present in a range of about 35%-57% by weight, about 40%-50% by weight of a water insoluble adjuvant, and a minor amount of an antioxidant, said masticatory substance having a softening end point for about 67°-76° C., an ash content of 46%, plus or minus 2%, and a maximum moisture content of about 1%.

46. The method of claim 40 wherein said medicament is pseudoephedrine.

47. The method of claim 40 wherein said medicament is indomethacin.

48. The method of claim 40 wherein said medicament is propranolol.

49. The method of claim 40 wherein said medicament is dimenhydrinate.

* * * * *